US012714330B2

(12) United States Patent
Park et al.

(10) Patent No.: US 12,714,330 B2
(45) Date of Patent: Aug. 25, 2026

(54) APPARATUS AND METHOD FOR OUTPUTTING ELECTROCARDIOGRAM SIGNAL AND RESPIRATION SIGNAL

(71) Applicant: MEZOO CO., LTD., Wonju-si (KR)

(72) Inventors: Junghwan Park, Wonju-si (KR); Sungpil Cho, Wonju-si (KR); Mihye Song, Wonju-si (KR); Hyunseok Choi, Wonju-si (KR); Sanghee Lee, Hongcheon-gun (KR)

(73) Assignee: MEZOO CO., LTD., Wonju-si (KR)

( * ) Notice: Subject to any disclaimer, the term of this patent is extended or adjusted under 35 U.S.C. 154(b) by 421 days.

(21) Appl. No.: 18/324,911

(22) Filed: May 26, 2023

(65) Prior Publication Data

US 2023/0301545 A1 Sep. 28, 2023

Related U.S. Application Data

(63) Continuation of application No. PCT/KR2022/018300, filed on Nov. 18, 2022.

(30) Foreign Application Priority Data

Jan. 11, 2022 (KR) ........................ 10-2022-0003958
Feb. 15, 2022 (KR) ........................ 10-2022-0019257

(51) Int. Cl.
*A61B 5/00* (2006.01)
*A61B 5/08* (2006.01)
(Continued)

(52) U.S. Cl.
CPC ............ *A61B 5/086* (2025.01); *A61B 5/0816* (2013.01); *A61B 5/318* (2021.01); *A61B 5/339* (2021.01); *A61B 5/6802* (2013.01)

(58) Field of Classification Search
CPC ....... A61B 5/0205; A61B 5/086; A61B 5/053; A61B 5/02438; A61B 5/0245;
(Continued)

(56) References Cited

U.S. PATENT DOCUMENTS 5,794,623 A * 8/1998 Forbes .................. A61B 5/341
600/513
8,487,772 B1 7/2013 Higgins
(Continued)

FOREIGN PATENT DOCUMENTS

CN 101365373 A 2/2009
CN 202568219 U 12/2012
(Continued)

OTHER PUBLICATIONS

A comparison of algorithms for estimation of a respiratory signal from the surface electrocardiogram, Computers in Biology and Medicine, vol. 37, Issue 3, pp. 305-314 (2007) (Year: 2007).*

*Primary Examiner* — Sana Sahand
(74) *Attorney, Agent, or Firm* — CANTOR COLBURN LLP

(57) ABSTRACT

Provided are a device and a method for outputting a respiration signal together with an electrocardiogram signal. The respiration signal output device includes an electrode signal measurement unit for measuring a signal between at least two electrodes attached to the body of a subject, a respiration signal generation unit for generating a respiration signal of the subject based on the measured signal, an electrocardiogram signal generation unit for generating an electrocardiogram signal of the subject based on the measured signal, and an output unit for outputting the electrocardiogram signal and the respiration signal.

9 Claims, 4 Drawing Sheets

(51) Int. Cl.

| | |
|---|---|
| ***A61B 5/085*** | (2006.01) |
| ***A61B 5/318*** | (2021.01) |
| ***A61B 5/339*** | (2021.01) |

(58) Field of Classification Search

CPC ......... A61B 5/0816; A61B 5/28; A61B 5/318; A61B 5/33; A61B 5/346; A61B 5/6802; A61B 5/683

See application file for complete search history.

(56) References Cited

U.S. PATENT DOCUMENTS

| | | | | |
|---|---|---|---|---|
| 8,888,700 | B2 | 11/2014 | Banet et al. | |
| 9,192,316 | B2 | 11/2015 | Hoskuldsson et al. | |
| 2007/0032733 | A1 | 2/2007 | Burton | |
| 2014/0309540 | A1 | 10/2014 | Morikawa et al. | |
| 2015/0150485 | A1* | 6/2015 | Fernando | A61B 5/0816 600/484 |
| 2021/0059606 | A1 | 3/2021 | Kim et al. | |

FOREIGN PATENT DOCUMENTS

| | | | |
|---|---|---|---|
| CN | 104771166 | A | 7/2015 |
| CN | 106618965 | A | 5/2017 |
| CN | 107374642 | A | 11/2017 |
| CN | 109984742 | A | 7/2019 |
| EP | 1999639 | B1 | 5/2018 |
| EP | 3440994 | A1 | 2/2019 |
| JP | S6141438 | A | 2/1986 |
| JP | 2018126511 | A | 8/2018 |
| KR | 20190016385 | | 2/2019 |
| KR | 20200024830 | | 3/2020 |
| KR | 20210024874 | | 3/2021 |
| KR | 102278695 | | 7/2021 |
| WO | 2014006891 | A1 | 1/2014 |

* cited by examiner (a)

(b)

APPARATUS AND METHOD FOR OUTPUTTING ELECTROCARDIOGRAM SIGNAL AND RESPIRATION SIGNAL

BACKGROUND

Field

The present disclosure relates to a device and a method for outputting an electrocardiogram signal and a respiration signal.

Description of the Related Art

Chronic obstructive pulmonary disease (COPD) is gradually increasing in prevalence in Korea due to high smoking rate and rapid aging, and is also a major chronic disease worldwide and a major cause of death. It is known that not only a decrease in lung capacity but also other factors, such as dysfunction of respiratory and exercise muscles, play an important role in a decrease in exercise ability in COPD patients. Respiratory rehabilitation is a customized treatment for each patient that is provided according to an individual condition based on evaluation in various ways, and requires all factors such as education, nutrition, and psychiatric treatment as well as just exercise. Through this, it is necessary to improve the physical and emotional states of patients with chronic lung disease and to maintain a health promotion state in the long term.

In addition, the most effective method for managing the progression of COPD is early diagnosis. Pulmonary function evaluation is useful for diagnosing respiratory diseases or for evaluating or managing pulmonary functions. For example, when a patient suffers from COPD, the pulmonary function evaluation may be regularly performed to measure the condition of the disease.

In addition, the measurement of respiratory flow parameters is one of tools for evaluating the respiratory ability of the patient. The parameters may include respiratory temperature, flow rate, volume, pressure, and respiratory function parameters that may be extracted from these measurements, such as respiratory rate, respiratory length and depth, apnea length, and time of inhalation and exhalation. The measurement is performed using non-direct measurement or direct respiration sensors that sense/measure/monitor actual respiratory flow.

There are several known methods and devices for measuring respiratory flow parameters. For example, like pulmometry and lung function tests that measure ventilation and the movement of air in and out of the lungs, a subject needs to artificially respire from the mouthpiece toward the sensor which rotates into the mouthpiece.

Meanwhile, in the case of non-ventilated patients in pulmometry and lung function tests that measure ventilation and the movement of air in and out of the lungs, there is a limitation that the patient awakes and recognizes, and it may only be applied as non-continuous monitoring that requires cooperation. In the case of a device that needs to be mounted on the face of the subject so that the sensor included in the device is located in the respiratory flow, the sensor needs to be placed on a mask covering the nostrils and mouth of the subject, which is inconvenient for the subject.

In addition, in the case of including a wearable sensor mounted on the face of the subject, there is a limitation in that a sensor position needs to be accurately placed on the face of the subject and finely adjusted in order to match the sensor to the respiratory flow.

Other known methods include devices that need to be mounted on the face of the subject so that the sensor included in the device is positioned in the respiratory flow. One example of these devices is a direct capnography. As another example, the device includes a wearable sensor mounted on the subject such that the sensor is positioned around the nostrils and adjacent to the mouth, for example, on the face/head.

On the other hand, a patient who is determined to have a problem in respiratory ability through the measurement of respiratory parameters performs respiratory rehabilitation under the monitoring of medical staffs in a self-exercise or hospital according to the condition of the patient.

In one conventional disclosure of handling a remote rehabilitation training medical device, there is described a technology for providing a system for home-based cardiac and respiratory rehabilitation treatment by measuring biosignals using a wearable device.

Respiratory rehabilitation aims to reduce acute deterioration by relieving symptoms of respiratory disease of the patient and improving exercise capacity through rehabilitation treatment in patients with respiratory diseases, and the respiratory rehabilitation is a personalized exercise prescription and is performed under the monitoring of medical staffs and evaluated through lung function tests.

In outpatient respiratory rehabilitation treatment, which is a commonly performed method, it requires at least 20 to 30 minutes at a time, 3 to 5 times a week, and a period of at least 6 to 8 weeks, and the patient needs to continue to visit during the treatment. Accordingly, there is a problem that the number of patients who may actually receive treatment is limited due to limitations in transportation and various conditions.

The background art of the present disclosure is disclosed in Korean Patent Registration No. 10-2278695.

SUMMARY

In order to solve the problems of the related art described above, an object of the present disclosure is to provide a wearable device that enables measurement of respiratory parameters by measuring impedance changes through a built-in sensor of a wearable or attachable types of electrocardiometer and does not cause inconvenience to users in performing the function of a pulmometer.

An object of the present disclosure is to solve the problems of the related art described above.

However, technical objects to be achieved by the exemplary embodiments of the present disclosure are not limited to the above-mentioned objects, and other technical objects may be present.

According to an exemplary embodiment of the present disclosure, there may be provided a respiration signal output device including an electrode signal measurement unit for measuring a signal between at least two electrodes attached to the body of a subject, a respiration signal generation unit for generating a respiration signal of the subject based on the measured signal, an electrocardiogram signal generation unit for generating an electrocardiogram signal of the subject based on the measured signal, and an output unit for outputting the electrocardiogram signal and the respiration signal.

The signal between the at least two electrodes may be an impedance signal, and the respiration signal generation unit may generate the respiration signal based on the impedance signal.

The impedance signal may represent a change in impedance that varies according to contraction and expansion of the muscles of the subject during respiration of the subject, and the respiration signal generation unit may detect the number of change values greater than a predetermined threshold value among a plurality of change values of the impedance signal included in a predetermined time interval and determine the respiratory rate of the subject based on the detected number of times, in which the respiration signal may include the respiratory rate.

In addition, the respiration signal generation unit may generate a respiration signal of the subject based on the electrocardiogram signal and the impedance signal.

The respiration signal generation unit may generate a respiration signal of the subject based on the impedance signal, and the respiration signal generation unit may change the generated respiration signal based on the electrocardiogram signal.

In addition, the respiration signal generation unit may change the generated respiration signal when it is determined that a measurement error issue of the subject has occurred based on the electrocardiogram signal.

In addition, the electrocardiogram signal generation unit may change the generated electrocardiogram signal based on the respiration signal.

In addition, the electrocardiogram signal generation unit may generate an electrocardiogram signal of the subject and a heart disease-related signal of the subject based on the measured signal, and change the heart disease-related signal based on the respiration signal.

In addition, the output unit may simultaneously display the electrocardiogram signal and the respiration signal on one display device.

According to another exemplary embodiment of the present disclosure, there is provided a respiration signal output method including the steps of: measuring a signal between at least two electrodes attached to the body of a subject; generating a respiration signal of the subject based on the measured signal; generating an electrocardiogram signal of the subject based on the measured signal; and outputting the electrocardiogram signal and the respiration signal.

The signal between the at least two electrodes may be an impedance signal, and in the generating of the respiration signal, the respiration signal may be generated based on the impedance signal.

In addition, the impedance signal may represent a change in impedance that varies according to contraction and expansion of the muscles of the subject during respiration of the subject, and in the generating of the respiration signal, the number of change values greater than a predetermined threshold value may be detected among a plurality of change values of the impedance signal included in a predetermined time interval and the respiratory rate of the subject is determined based on the detected number of times, in which the respiration signal may include the respiratory rate.

In addition, in the generating of the respiration signal, a respiration signal of the subject may be generated based on the electrocardiogram signal and the impedance signal.

In addition, in the outputting, the electrocardiogram signal and the respiration signal may be simultaneously displayed on one display device.

In addition, in the generating of the respiration signal, a respiration signal of the subject may be generated based on the impedance signal, and in the generating of the respiration signal, the generated respiration signal may be changed based on the electrocardiogram signal.

The above-mentioned technical solutions are merely exemplary and should not be construed as limiting the present disclosure. In addition to the above-described exemplary embodiments, additional exemplary embodiments may exist in the drawings and detailed description of the disclosure.

The above-described solving means are merely illustrative but should not be construed as limiting the present disclosure. In addition to the above-described embodiments, additional embodiments may be further provided in the drawings and the detailed description of the present disclosure.

According to the exemplary embodiment of the present disclosure, it is possible to provide a wearable device that performs the function of a pulmometer without inconvenience of use by detecting changes in impedance through a built-in sensor of a wearable electrocardiograph to measure respiratory flow parameters.

Further, continuous respiratory parameter information obtained through the wearable electrocardiograph allows medical staffs to easily monitor patients undergoing home respiratory rehabilitation.

In addition, since the respiratory information measured by the wearable electrocardiograph shows the change in respiratory rate over time as a graph, when medical staffs monitor a patient undergoing home respiratory rehabilitation, it may be possible to evaluate the rehabilitation performance of the patient and a resulting effect not only in real time but also at a predetermined time after rehabilitation.

However, effects obtainable herein are not limited to the effects described above, and other effects may be present.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE EMBODIMENT

Figure 1:
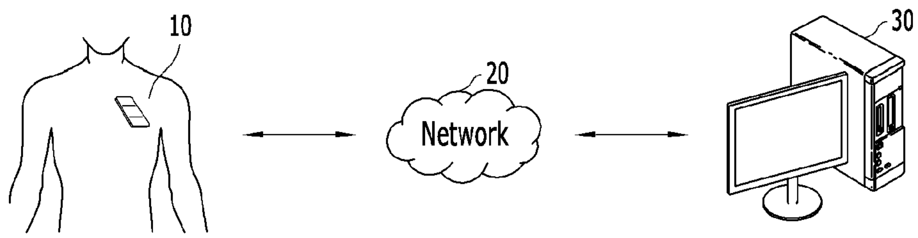
FIG. 1 is a schematic configuration diagram of a respiration signal output system according to an exemplary embodiment of the present disclosure.

Hereinafter, exemplary embodiments of the present disclosure will be described in detail so as to be easily implemented by those skilled in the art, with reference to the accompanying drawings. However, the present disclosure may be embodied in many different forms and are not limited to the exemplary embodiments to be described herein. In addition, parts not related with the description have been omitted in order to clearly describe the present disclosure in the drawings and throughout the present specification, like reference numerals designate like elements.

Throughout this specification, when a certain part is "connected" with the other part, it is meant that the certain part may be "directly connected" with the other part and "electrically connected" with the other part with another element interposed therebetween.

Throughout the present specification, it will be understood that when a certain member is located "on", "above", "at the top of", "under", "below", and "at the bottom of" the other member, a certain member is in contact with the other member and another member may also be present between the two members.

Throughout the specification, when a part "comprises" a component, it will be understood to further include another component, not the exclusion of another component unless explicitly described to the contrary.

The present disclosure relates to respiration signal output device 10 and method.

FIG. 1 is a schematic configuration diagram of a respiration signal output system 1000 according to an exemplary embodiment of the present disclosure.

Referring to FIG. 1, the respiration signal output system 1000 according to an exemplary embodiment of the present disclosure may include a respiration signal output device 10 and a display device 30 according to an exemplary embodiment of the present disclosure. In addition, the respiration signal output device 10 of the respiration signal output system 1000 may include an electrode signal measurement unit 110, an electrocardiogram signal generation unit 130, a respiration signal generation unit 120, and an output unit 140.

In the description of the exemplary embodiment of the present disclosure, the display device 30 may be a device for acquiring and outputting various kinds of information, such as heart disease-related information, lung capacity information, home respiratory rehabilitation information, and respiratory information of a subject. For example, the display device 30 may be a device owned by a subject who manipulates the respiration signal output device 10 or a device owned by an administrator in a position to monitor information output by the respiration signal output device 10. As another example, the display device 30 is integrally provided with the respiration signal output device 10, and may refer to a user manipulation module including an input interface for receiving health information of a subject from the respiration signal output device 10, and an output interface for outputting various types of information.

The respiration signal output device 10 and the display device 30 may communicate with each other via a network 20. The network 20 means a connection structure in which information is exchangeable between respective nodes such as terminals and servers. Examples of the network 20 include a 3rd generation partnership project (3GPP) network, a long term evolution (LTE) network, a 5G network, a world interoperability for microwave access (WIMAX) network, internet, a local area network (LAN), a wireless local area network (Wireless LAN), a wide area network (WAN), a personal area network (PAN), a WiFi network, a Bluetooth network, a satellite broadcasting network, an analog broadcasting network, and a digital multimedia broadcasting (DMB) network, but are not limited thereto.

Figure 2:
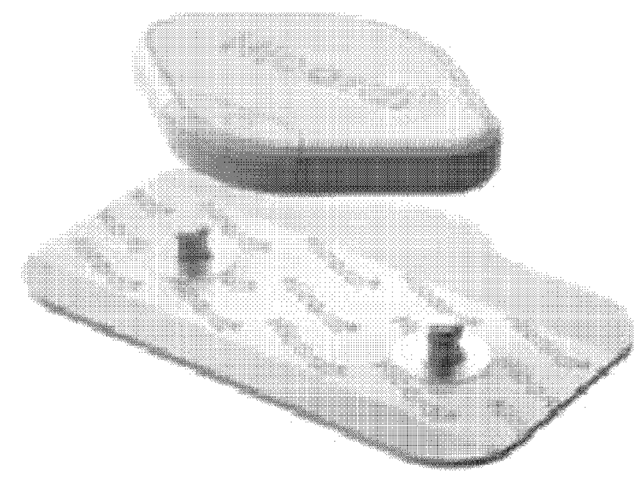
FIG. 2 is a diagram illustrating a configuration of a respiration signal output device according to an exemplary embodiment of the present disclosure.

FIG. 2 is a diagram illustrating a configuration of the respiration signal output device according to an exemplary embodiment of the present disclosure.

Referring to FIG. 2, the respiration signal output device 10 according to an exemplary embodiment of the present disclosure may be configured by a wearable device including at least two protruding electrodes and an electrode patch including contact electrodes electrically connected to the at least two protruding electrodes.

The wearable device may be formed in a flat shape of the form such as a circle, an ellipse, or a rectangle, or a polyhedral shape of the form including a cylinder, or a triangular prism, and may be provided in various shapes suitable for the purpose and application field. The shape of the wearable device is not limited to the drawings, and it is applicable for any shape having one surface on which the protruding electrodes may be formed so as to come into contact with the contact electrodes of the electrode patch.

In an exemplary embodiment of the present disclosure, the electrode patch is a component that is attached to the body of the subject and electrically connected to the wearable device, and may be made of a flexible material having wires formed therein. Accordingly, since the electrode patch may be bent or curved freely, the electrode patch may be easily attached to a curved body.

Figure 3:
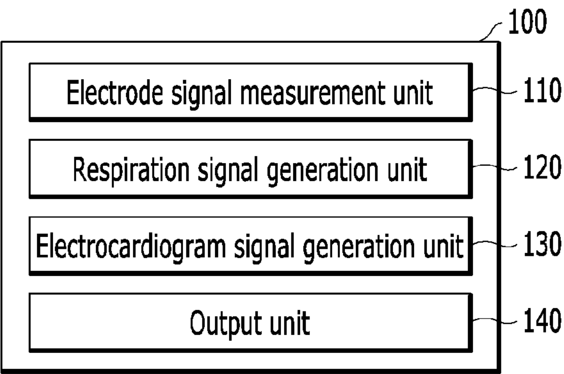
FIG. 3 is a schematic block diagram of a respiration signal output device according to an exemplary embodiment of the present disclosure.
Figure 4:
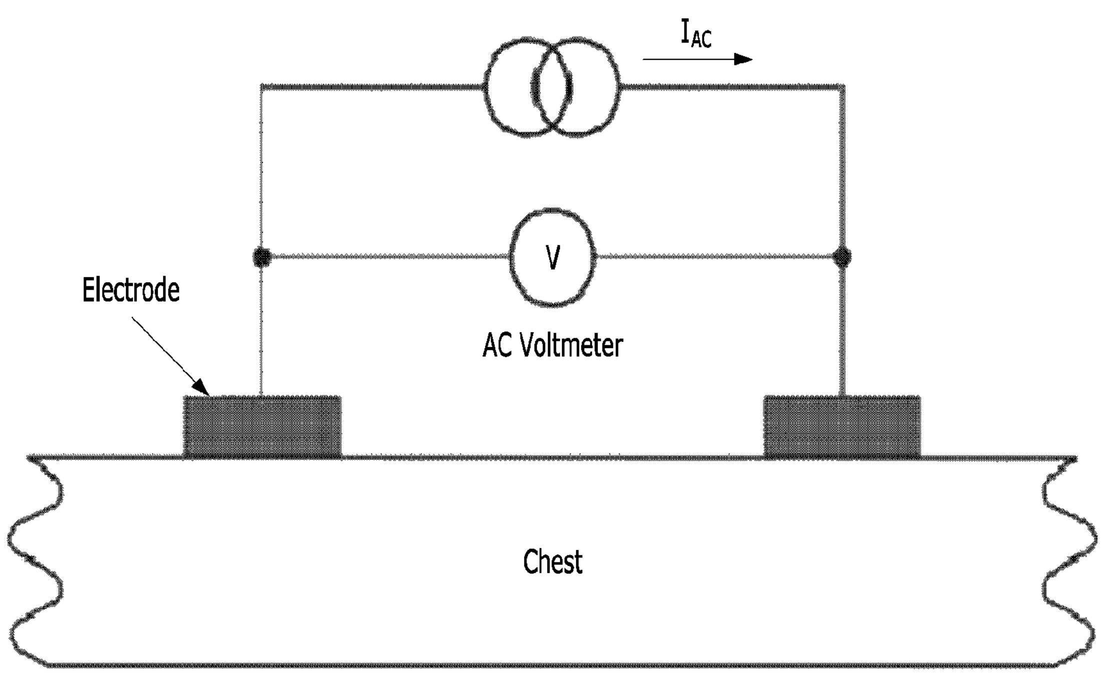
FIG. 4 is a diagram illustrating an electrode for measuring impedance in the respiration signal output device according to an exemplary embodiment of the present disclosure.

FIG. 3 is a schematic block diagram of the respiration signal output device 10 according to an exemplary embodiment of the present disclosure.

The respiration signal output device 10 according to an exemplary embodiment of the present disclosure may include an electrode signal measurement unit 110 for measuring a signal between at least two electrodes attached to the body of a subject, a respiration signal generation unit 120 for generating a respiration signal of the subject based on the measured signal, an electrocardiogram signal generation unit 130 for generating an electrocardiogram signal of the subject based on the measured signal, and an output unit 140 for outputting the electrocardiogram signal and the respiration signal.

According to an exemplary embodiment of the present disclosure, the electrode signal measurement unit 110 may measure a signal between at least two electrodes attached to the body of the subject.

Specifically, the electrode signal measurement unit 110 may measure an impedance signal between at least two electrodes.

In addition, during inspiration, the amount of gas in the chest increases compared to the amount of body fluid so that the conductivity reduces, and the length of the conduction path increases during inspiration to increase the impedance. A change in impedance (i.e., respiration impedance) may generate a voltage component that varies upon current injection, and determine respiration information of the subject through the variable voltage component.

According to an exemplary embodiment of the present disclosure, the respiration signal generation unit 120 may generate a respiration signal of the subject based on the measured signal between the two or more electrodes.

Specifically, the respiration signal generation unit 120 may generate a respiration signal based on the impedance signal. The impedance signal may be a signal indicating a change in impedance that varies according to contraction and expansion of muscles during respiration of the subject based on a relatively constant value of baseline impedance.

In addition, the respiration signal generation unit 120 may detect the number of change values greater than a predetermined threshold value among a plurality of change values of the impedance signal included in a predetermined time interval, and determine the respiratory rate of the subject based on the detected number of times, and the respiratory rate may be included in the respiration signal.

Specifically, the respiration signal generation unit 120 measures a plurality of impedance signals changed at a predetermined cycle for a predetermined time. The signal generation unit 120 counts a number of which is greater than or equal to the threshold value, when the magnitude of the measured signal is above the threshold value. Conversely, the signal generation unit 120 does not count the number when the magnitude of the measured signal is below the threshold value. Doing this, the respiration rate is determined and a respiration signal may be generated.

In addition, the respiration signal generation unit 120 may generate the respiration signal of the subject based on the electrocardiogram signal and the impedance signal.

Specifically, the respiration signal generation unit 120 may generate a respiration signal for respiratory parameters including at least one of a respiratory sufficiency index, a ventilation rate per minute, a respiratory rate, a tidal volume, an inspiratory parameter, an expiratory parameter, a respiratory volume, and a respiratory flow of the subject based on the electrocardiogram signal and the impedance signal.

In addition, the respiration signal generation unit 120 may generate a respiration signal corresponding to each respiratory parameter based on the electrocardiogram signal and the impedance signal over time.

In addition, the respiration signal generation unit 120 may change the generated respiration signal based on the electrocardiogram signal.

Specifically, the respiration signal generation unit 120 may change the respiration signal into a first respiration signal and a second respiration signal according to the order of respiratory parameters having a large change amount based on the interval and intensity of the electrocardiogram signal.

For example, when an electrocardiogram signal of irregular heart rate, low heart rate, or high heart rate is measured, the respiratory rate with the largest change amount may be changed into the first respiration signal, and then the respiratory volume with the large change amount may be changed into the second respiration signal.

In addition, the respiration signal generation unit 120 may change the generated respiration signal when it is determined that a measurement error issue of the subject has occurred based on the electrocardiogram signal.

For example, the respiration signal generation unit 120 may change the generated respiration signal to a respiration signal requesting re-measurement when the electrocardiogram signal of irregular heart rate, low heart rate, or high heart rate is measured.

According to an exemplary embodiment of the present disclosure, the electrocardiogram signal generation unit 130 may generate an electrocardiogram signal of a subject based on the measured signal between two or more electrodes.

Specifically, the electrocardiogram signal generation unit 130 may generate an electrocardiogram signal of the subject based on a change in voltage value according to a change in impedance measured from two or more electrodes for a preset time period.

Further, when there is a waveform in which a signal belonging to the threshold range is generated for a preset time among waveforms of the acquired electrocardiogram signal, a signal corresponding to the corresponding waveform, that is, a signal corresponding to a waveform satisfying a predetermined characteristic condition may be determined as an abnormal suspected electrocardiogram signal that is likely to be an abnormal electrocardiogram signal.

In addition, the electrocardiogram signal generation unit 130 may change the generated electrocardiogram signal based on the respiration signal.

Specifically, the electrocardiogram signal generation unit 130 may change a first electrocardiogram signal that is a normal electrocardiogram signal and a second electrocardiogram signal that is an abnormal electrocardiogram signal based on each parameter included in the respiration signal.

For example, the electrocardiogram signal generation unit 130 may change the electrocardiogram signal to a first electrocardiogram signal that is a normal electrocardiogram signal in the case in which each respiratory parameter is measured within a preset range, and change the electrocardiogram signal to a second electrocardiogram signal that is an abnormal electrocardiogram in the case that each respiration signal is measured out of the preset range.

In addition, the electrocardiogram signal generation unit 130 may generate an electrocardiogram signal of the subject and a heart disease-related signal of the subject based on the measured signal, and change the heart disease-related signal based on the respiration signal.

Specifically, when an electrical signal having a first voltage value or more and a second voltage value or less among the electrocardiogram signals obtained from the respiration signal output device 10 is generated for a predetermined time, the electrocardiogram signal generation unit 130 may generate a heart disease-related signal by determining the corresponding signal as the abnormal suspected electrocardiogram signal.

In addition, after the first determination as the abnormal suspected electrocardiogram signal, the electrocardiogram signal generation unit 130 may secondly determine whether the abnormal suspected electrocardiogram signal is the abnormal electrocardiogram signal, based on similarity comparison between waveform data of a plurality of respiration signals and a plurality of abnormal electrocardiogram signals previously stored in a database (not illustrated) and waveform data of abnormal suspected electrocardiogram signals. The electrocardiogram signal generation unit 130 may change the heart disease-related signal based on the secondary determination result and the respiration signal.

According to an exemplary embodiment of the present disclosure, the output unit 140 may output the electrocardiogram signal and the respiration signal.

Specifically, the output unit 140 may output the electrocardiogram signal and the respiration signal on a device owned by a subject who manipulates the respiration signal output device 10 or the display device 30 owned by an administer that monitors information outputted by the respiration signal output device 10.

In addition, the output unit 140 may simultaneously display the electrocardiogram signal and the respiration signal on one display device 30.

Figure 5:
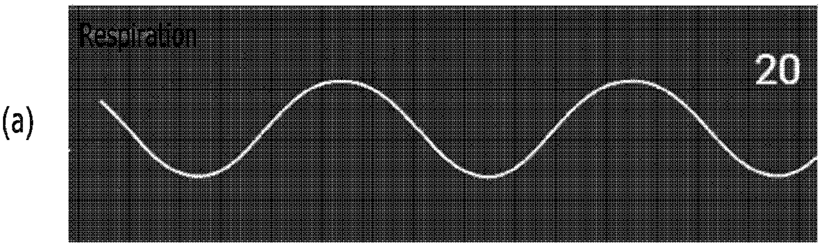
FIG. 5 is a diagram illustratively illustrating results of outputting an electrocardiogram signal and respiration information on a display device according to an exemplary embodiment of the present disclosure.
Figure 5:
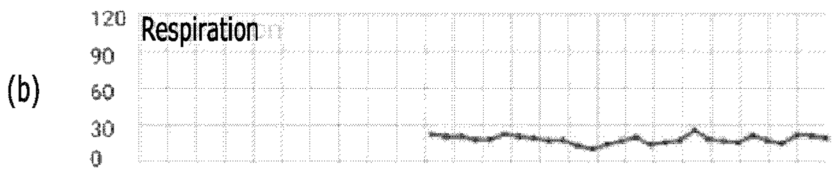

In this regard, FIG. 5 is a diagram illustratively illustrating results of outputting an electrocardiogram signal and respiration information on the display device 30 according to an exemplary embodiment of the present disclosure.

Referring to FIG. 5A, for example, the output unit 140 may output an electrocardiogram signal and continuous respiratory rate information measured through the respiration signal output device 10.

Specifically, the output unit 140 may output changes in the electrocardiogram and each respiratory parameter included in the respiration signal on the display device 30.

In addition, referring to FIG. 5B, the output unit 140 may output a change in respiratory rate over time measured through the respiration signal output device 10.

Specifically, the output unit 140 may output changes in each respiratory parameter included in the respiration signal over time on the display device 30.

In addition, the output unit 140 may output on the display device 30 respiratory parameters greater than or equal to or less than set values to be easily identified for each respiratory parameter which is set to a predetermined value by a user input earlier than other respiratory parameters.

With the configuration as described above, the user may not only set an abnormal health signal section, but also monitor a patient more accurately based on the electrocardiogram signal and the respiration signal displayed on one screen.

Figure 6:
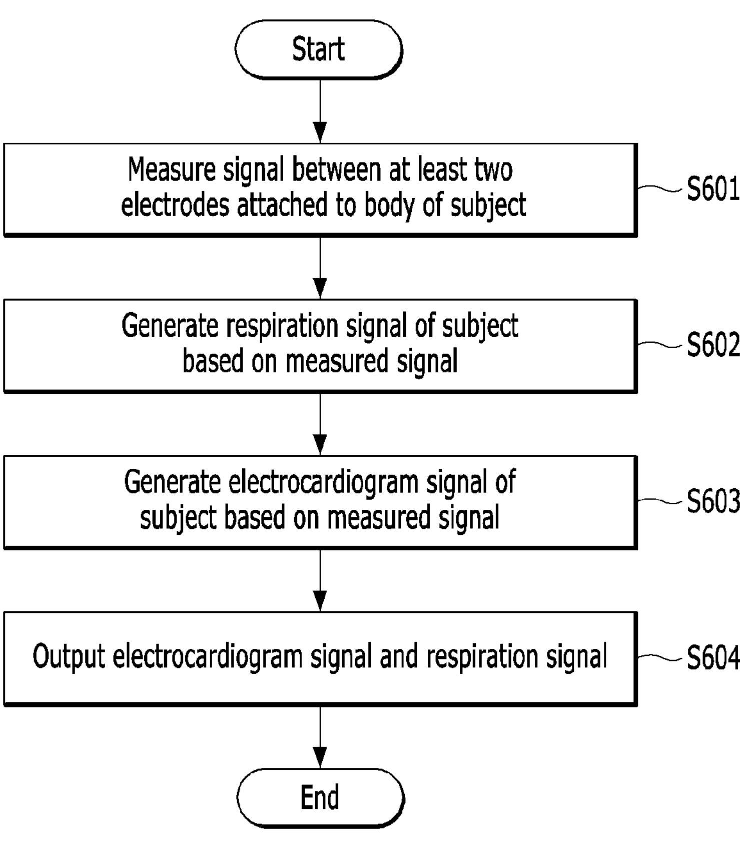
FIG. 6 is an operational flowchart of a respiration signal output method according to an exemplary embodiment of the present disclosure.

FIG. 6 is an operational flowchart of a respiration signal output method according to an exemplary embodiment of the present disclosure.

The respiration signal output method illustrated in FIG. 6 may be performed by the respiration signal output device 10 described above. Accordingly, even if the content is omitted below, the description on the respiration signal output device 10 may be equally applied even to the description on the respiration signal output method.

Referring to FIG. 6, in step S601, the electrode signal measurement unit 110 may measure a signal between at least two electrodes attached to the body of a subject.

Next, in step S602, the respiration signal generation unit 120 may generate a respiration signal of the subject based on the measured signal.

Next, in step S603, the electrocardiogram signal generation unit 130 may generate an electrocardiogram signal of the subject based on the measured signal.

Next, in step S604, the output unit 140 may output the electrocardiogram signal and the respiration signal.

In the above description, steps S601 to S604 may be further divided into additional steps or combined with fewer steps according to an exemplary embodiment of the present disclosure. In addition, some steps may also be omitted if necessary, or the order between the steps may also be changed.

The respiration signal output method according to the exemplary embodiment of the present disclosure may be implemented in a form of program instructions which may be performed through various computer means to be recorded in a computer readable medium. The computer readable medium may include program instructions, data files, and data structures, alone or in combination. The program instructions recorded in the medium may be specially designed and configured for the present disclosure, or may be publicly known to and used by those skilled in the computer software art. Examples of the computer readable medium include magnetic media, such as a hard disk, a floppy disk, and a magnetic tape, optical media such as a CD-ROM and a DVD, magneto-optical media such as a floptical disk, and hardware devices such as a ROM, a RAM, and a flash memory, which are specially configured to store and execute the program instructions. Examples of the program instructions include high language codes executable by a computer using an interpreter, as well as machine language codes created by a compiler. The hardware device may be configured to be operated with one or more software modules in order to perform the operation of the present disclosure and vice versa.

Further, the aforementioned respiration signal output method may be implemented even in the form of computer programs or applications to be executed by a computer, which are stored in the recording medium.

The aforementioned description of the present disclosure is to be exemplified, and it will be understood by those skilled in the art that the present disclosure may be easily modified in other detailed forms without changing the technical spirit or required features of the present disclosure. Therefore, it should be appreciated that the exemplary embodiments described above are illustrative in all aspects and are not restricted. For example, each component explained in a singular form may be distributed and carried out, likewise, components explained in a distributed form may also be carried out in a combined form.

The scope of the present disclosure is represented by appended claims to be described below rather than the detailed description, and it is to be interpreted that the meaning and scope of the claims and all the changes or modified forms derived from the equivalents thereof come within the scope of the present disclosure.

What is claimed is:

1. A respiration signal output device for outputting a respiration signal together with an electrocardiogram signal, the respiration signal output device comprising:

an electrode signal measurement unit configured to measure a signal between at least two electrodes attached to the body of a subject, wherein the measured signal includes an impedance signal;

a respiration signal generation unit configured to generate a respiration signal of the subject based on the impedance signal;

an electrocardiogram signal generation unit configured to generate an electrocardiogram signal of the subject based on the impedance signal; and an output unit configured to output the electrocardiogram signal and the respiration signal, wherein the respiration signal generation unit is configured to change the generated respiration signal based on the electrocardiogram signal, and wherein the electrocardiogram signal generation unit is configured to change the generated electrocardiogram signal based on the respiration signal.

2. The respiration signal output device of claim 1, wherein the impedance signal represents a change in impedance that varies according to contraction and expansion of the muscles of the subject during respiration of the subject, and the respiration signal generation unit detects the number of change values greater than a predetermined threshold value among a plurality of change values of the impedance signal included in a predetermined time interval and determines a respiratory rate of the subject based on the detected number of times, wherein the respiration signal includes the respiratory rate.

3. The respiration signal output device of claim 1, wherein the respiration signal generation unit changes the generated respiration signal when it is determined that a measurement error issue of the subject has occurred based on the electrocardiogram signal.

4. The respiration signal output device of claim 1, wherein the electrocardiogram signal generation unit generates the electrocardiogram signal of the subject and a heart disease-related signal of the subject based on the measured signal, and changes the heart disease-related signal based on the respiration signal.

5. The respiration signal output device of claim 1, wherein the output unit simultaneously displays the electrocardiogram signal and the respiration signal on a single display device.

6. A respiration signal output method for outputting a respiration signal together with an electrocardiogram signal, the method comprising the steps of:

measuring a signal between at least two electrodes attached to the body of a subject, wherein the measured signal includes an impedance signal;

generating a respiration signal of the subject based on the impedance signal;

generating an electrocardiogram signal of the subject based on the impedance signal; and outputting the electrocardiogram signal and the respiration signal, wherein, in the generating of the respiration signal, the generated respiration signal is changed based on the electrocardiogram signal, and wherein in the generating of the electrocardiogram signal, the generated electrocardiogram signal is changed based on the respiration signal.

7. The respiration signal output method of claim 6, wherein the impedance signal represents a change in impedance that varies according to contraction and expansion of the muscles of the subject during respiration of the subject, and in the generating of the respiration signal, the number of change values greater than a predetermined threshold value is detected among a plurality of change values of the impedance signal included in a predetermined time interval, and a respiratory rate of the subject is determined based on the detected number of times, wherein the respiration signal includes the respiratory rate.

8. The respiration signal output method of claim 6, wherein in the outputting, the electrocardiogram signal and the respiration signal are simultaneously displayed on a single display device.

9. A non-transitory computer readable recording medium recording programs for executing the method of claim 6 in a computer.

* * * * *